United States Patent [19]
Okuda et al.

[11] Patent Number: 4,791,128
[45] Date of Patent: Dec. 13, 1988

[54] RHIZOXIN ESTERS AND SALTS, THEIR PHARMACEUTICAL USE AS ANTI-TUMOR AGENTS

[75] Inventors: Shigenobu Okuda; Shigeo Iwasaki, both of Tokyo; Michio Namikoshi, Kokubunji; Masao Arakawa; Fusaaki Shimizu, both of Hiromachi, all of Japan

[73] Assignee: Sankyo Company Limited, Tokyo, Japan

[21] Appl. No.: 143,314

[22] Filed: Jan. 11, 1988

Related U.S. Application Data

[63] Continuation of Ser. No. 833,883, Feb. 25, 1986, abandoned.

[30] Foreign Application Priority Data

Feb. 28, 1985 [JP] Japan ................................ 60-39399

[51] Int. Cl.$^4$ ..................... A61K 31/42; C07D 493/22
[52] U.S. Cl. .................................. 514/374; 548/235; 548/236
[58] Field of Search ................ 548/235, 236; 514/374

[56] References Cited

FOREIGN PATENT DOCUMENTS 145177  6/1985  European Pat. Off. ............ 514/374

OTHER PUBLICATIONS

Abstract of the Proceedings of the Cancer Society, Oct., 1984.
Paper sheets for "Poster Session" International Chemical Congress of the Pacific Basin Society Dec. 18, 1984, Honolulu, Hawaii.
The Merck Index, Tenth Edition, 1983, 9650, Undecylenic Acid.
National Inst. of Agro–Environmental Sciences, CA 103–1061576.
Iwasaki et al., J. Antibiotics, 37, 354 (1984).

*Primary Examiner*—Donald G. Daus
*Assistant Examiner*—Cecilia Shen
*Attorney, Agent, or Firm*—Frishauf, Holtz, Goodman & Woodward

[57] ABSTRACT

Acylated derivatives of rhizoxin and of rhizoxin-2-ene may be prepared by reacting rhizoxin or rhizoxin-2-ene with an acid or reactive derivative thereof. They have excellent anti-tumor activity.

27 Claims, No Drawings

RHIZOXIN ESTERS AND SALTS, THEIR PHARMACEUTICAL USE AS ANTI-TUMOR AGENTS

This application is a continuation of application Ser. No. 833,883, filed Feb. 25, 1986, now abandoned.

BACKGROUND TO THE INVENTION

The present invention relates to a series of novel derivatives of the compound rhizoxin. The invention also provides a process for preparing such compounds and methods and compositions for using them.

Rhizoxin itself is a known substance having the following formula:

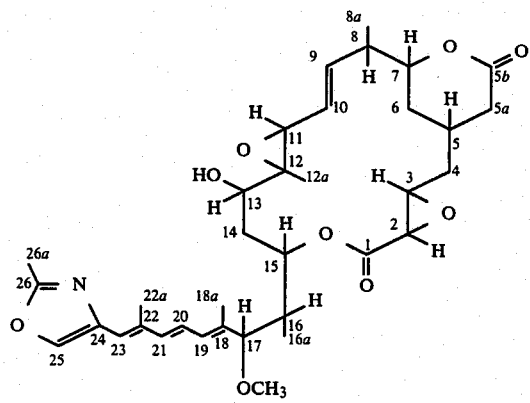

Rhizoxin itself and its acetate were disclosed in J. Antibiotics, 37, 354 (1984) and the anti-tumor activity of rhizoxin was disclosed in the Abstracts of the 43rd General Meeting of the Japanese Cancer Society, page 243, Title No. 1005 (1984).

Rhizoxin-2-ene was reported on Dec. 18th, 1984 to the 1984 International Chemical Congress of the Pacific Basin Society, Honolulu, Hawaii.

We have now discovered a series of rhizoxin derivatives which have far better anti-tumor activity than rhizoxin and its acetate and which have a lower toxicity than rhizoxin itself.

BRIEF SUMMARY OF INVENTION

The compounds of the present invention are those compounds of formula (I):

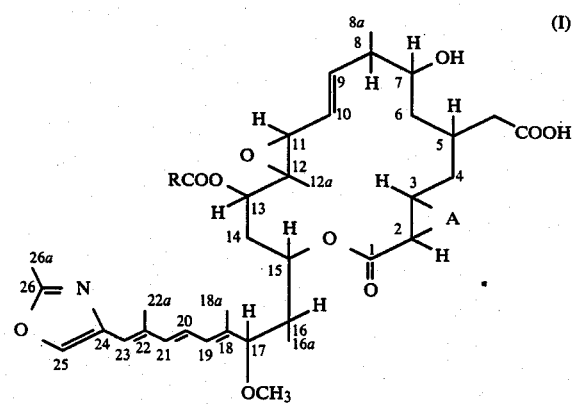

wherein:

R represents an alkyl group having at least 2 carbon atoms; and

A represents an extra carbon-carbon bond or an oxygen atom, and pharmaceutically acceptable salts and ring-closed lactones thereof.

The ring-closed lactone corresponding to the compound of formula (I) may be represented by the formula (II):

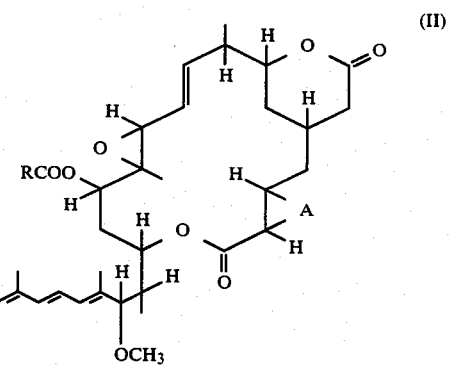

wherein R and A are as defined above.

Compounds of formula (II) may be prepared by reacting a compound of formula (III):

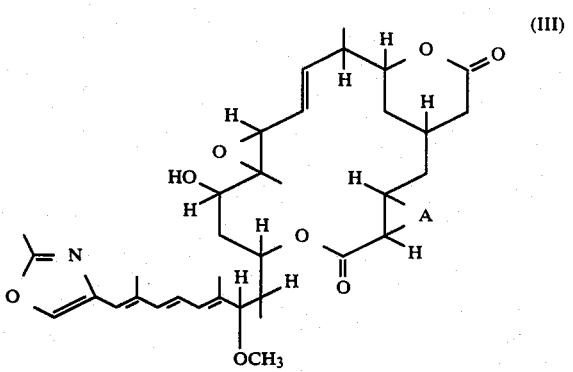

(wherein A is as defined above) with a carboxylic acid of formula (IV):

RCOOH        (IV)

(wherein R is as defined above) or a reactive derivative thereof.

Salts of the compounds of formula (I) may be prepared by reacting the compound of formula (II) with an appropriate base. The free acid of formula (I) may be prepared by reacting such a salt with an acid.

The invention also provides a pharmaceutical composition comprising an anti-tumor agent in admixture with a pharmaceutically acceptable carrier or diluent. wherein the anti-tumor agent is at least one compound selected from the group consisting of compounds of formula (I), compounds of formula (II) and pharmaceutically acceptable salts of said compounds of formula (I).

The invention still further provides a method of treating an animal, especially mammal, including human being, suffering from tumors, by administering thereto an effective amount of an anti-tumor agent, wherein said anti-tumor agent is at least one compound selected from the group consisting of compounds of formula (I), compounds of formula (II) and pharmaceutically acceptable salts of said compounds of formula (I).

DETAILED DESCRIPTION OF INVENTION

In the compounds of the invention, R represents an alkyl group having at least 2 carbon atoms. Such an alkyl group may be a straight or branched chain group and there is, in principle, no upper limit, beyond the practical one of the availability of the relevant corresponding acid, to the number of carbon atoms which such an alkyl group may contain. In most cases, a practical upper limit is probably about 40 carbon atoms, more preferably about 30 carbon atoms. Examples of such groups include the ethyl, propyl, isopropyl, butyl, sec-butyl, isobutyl, t-butyl, pentyl, isopentyl, neopentyl, t-pentyl, hexyl, 1-methylpentyl, 2-methylpentyl, 3-methylpentyl, isohexyl, heptyl, 1-methylhexyl, 2-methylhexyl, 5-methylhexyl, 3-ethylpentyl, octyl, 2-methylheptyl, 6-methylheptyl, 2-ethylhexyl, 2-ethyl-3-methylpentyl, 3-ethyl-2-methylpentyl, nonyl, 2-methyloctyl, 7-methyloctyl, 4-ethylheptyl, 3-ethyl-2-methylhexyl, 2-ethyl-1-methylhexyl, decyl, 2-methylnonyl, 8-methylnonyl, 5-ethyloctyl, 3-ethyl-2-methylheptyl, 3,3-diethylhexyl, undecyl, 2-methyldecyl, 9-methyldecyl, 4-ethylnonyl, 3,5-dimethylnonyl, 3-propyloctyl, 5-ethyl-4-methyloctyl, dodecyl, 1-methylundecyl, 10-methylundecyl, 3-ethyldecyl, 5-propylnonyl, 3,5-diethyloctyl, tridecyl, 11-methyldodecyl, 7-ethylundecyl, 4-propyldecyl, 5-ethyl-3-methyldecyl, 3-pentyloctyl, tetradecyl, 12-methyltridecyl, 8-ethyldodecyl, 6-propylundecyl, 4-butyldecyl, 2-pentylnonyl, pentadecyl, 13-methyltetradecyl, 10-ethyltridecyl, 7-propyldodecyl, 5-ethyl-3-methyldodecyl, 4-pentyldecyl, hexadecyl, 14-methylpentadecyl, 6-ethyltetradecyl, 4-propyltridecyl, 2-butyldodecyl, heptadecyl, 15-methylhexadecyl, 7-ethylpentadecyl, 3-propyltetradecyl, 5-pentyldodecyl, octadecyl, 16-methylheptadecyl, 5-propylpentadecyl, nonadecyl, 17-methyloctadecyl, 4-ethylheptadecyl, icosyl, 18-methylnonadecyl, 3-ethyloctadecyl, henicosyl, docosyl, tricosyl, tetracosyl and pentacosyl groups. Of these groups, we prefer the $C_3$–$C_{17}$, more preferably the $C_7$–$C_{13}$, alkyl groups, whether straight or branched chain groups.

Compounds of formula (I) are free acids and hence can form salts with bases. Provided that the resulting salt is pharmaceutically acceptable, which, as is well-known in the art, means that the salt does not have reduced (or unacceptably reduced) activity or increased (or unacceptably increased) toxicity as compared with the parent acid, there is no restriction on the nature of the cation forming the salt. Examples of suitable salts include metal salts, salts with amino acids and salts with ammonia and organic amines. Examples of suitable metal salts include salts with: alkali metals, such as sodium or potassium; alkaline earth metals, such as calcium or magnesium; and salts with other pharmaceutically acceptable metals, such as aluminum, iron, zinc, copper, nickel and cobalt. However, the preferred salts are those with alkali metals, alkaline earth metals and aluminum, and the most preferred salts are the sodium, potassium, calcium and aluminum salts. Examples of amino acids with which the compounds of formula (I) may form salts include such basic amino acids as arginine, lysine, histidine, α,γ-diaminobutyric acid and ornithine. Examples of amines with which the compounds of formula (I) may form salts include t-octylamine, dibenzylamine, dicyclohexylamine, morpholine, D-phenylglycine alkyl esters and D-glucosamine.

In naming the compounds of the invention, they are named semi-systematically in accordance with the recommendations of the International Union of Pure and Applied Chemistry, "Nomenclature of Organic Chemistry" Section F, taking rhizoxin as the base name.

Thus, compounds of formula (II) where A represents an oxygen atom are simply esters of rhizoxin with an acid of formula RCOOH and these are thus named as rhizoxin-13-yl acylates. The ring-opened analog of rhizoxin is called rhizoxin-5b-oic acid and thus compounds of formula (I) where A represents an oxygen atom are named as the 13-acyloxy derivatives of this, i.e. 13-acyloxy-13-dehydroxyrhizoxin-5b-oic acids.

Compounds of formula (II) where A represents an extra carbon-carbon bond are regarded as derivatives of rhizoxin-2-ene, more formally 2,3-deoxyrhizoxin-2-ene. Hence, compounds of formulae (I) and (II) where A represents such a bond are named as 13-acyloxy-13-dehydroxy-2,3-deoxyrhizoxin-2-en-5b-oic acids and 2,3-deoxyrhizoxin-2-en-13-yl acylates, respectively.

Examples of compounds of the present invention are given in the following list and the compounds of the invention are hereinafter, where appropriate, identified by the numbers assigned to them in this list.

1. 13-butyryloxy-13-dehydroxyrhizoxin-5b-oic acid
2. rhizoxin-13-yl butyrate
3. 13-valeryloxy-13-dehydroxyrhizoxin-5b-oic acid
4. rhizoxin-13-yl valerate
5. 13-isovaleryloxy-13-dehydroxyrhizoxin-5b-oic acid
6. rhizoxin-13-yl isovalerate
7. 13-hexanoyloxy-13-dehydroxyrhizoxin-5b-oic acid
8. rhizoxin-13-yl hexanoate
9. 13-(3,3-dimethylbutyryloxy)-13-dehydroxyrhizoxin-5b-oic acid
10. rhizoxin-13-yl 3,3-dimethylbutyrate
11. 13-heptanoyloxy-13-dehydroxyrhizoxin-5b-oic acid
12. rhizoxin-13-yl heptanoate
13. 13-(5-methylhexanoyloxy)-13-dehydroxyrhizoxin-5b-oic acid
14. rhizoxin-13-yl 5-methylhexanoate
15. 13-(4-methylhexanoyloxy)-13-dehydroxyrhizoxin-5b-oic acid
16. rhizoxin-13-yl 4-methylhexanoate
17. 13-octanoyloxy-13-dehydroxyrhizoxin-5b-oic acid
18. rhizoxin-13-yl octanoate
19. 13-(6-methylheptanoyloxy)-13-dehydroxyrhizoxin-5b-oic acid
20. rhizoxin-13-yl 6-methylheptanoate
21. 13-(4-ethylhexanoyloxy)-13-dehydroxyrhizoxin-5b-oic acid
22. rhizoxin-13-yl 4-ethylhexanoate
23. 13-nonanoyloxy-13-dehydroxyrhizoxin-5b-oic acid
24. rhizoxin-13-yl nonanoate
25. 13-(4-ethyl-3-methylhexanoyloxy)-13-dehydroxyrhizoxin-5b-oic acid
26. rhizoxin-13-yl 4-ethyl-3-methylhexanoate
27. 13-(7-methyloctanoyloxy)-13-dehydroxyrhizoxin-5b-oic acid
28. rhizoxin-13-yl 7-methyloctanoate
29. 13-decanoyloxy-13-dehydroxyrhizoxin-5b-oic acid
30. rhizoxin-13-yl decanoate
31. 13-(8-methylnonanoyloxy)-13-dehydroxyrhizoxin-5b-oic acid
32. rhizoxin-13-yl 8-methylnonanoate
33. 13-(5-ethyloctanoyloxy)-13-dehydroxyrhizoxin-5b-oic acid 34. rhizoxin-13-yl 5-ethyloctanoate
35. 13-undecanoyloxy-13-dehydroxyrhizoxin-5b-oic acid
36. rhizoxin-13-yl undecanoate
37. 13-(9-methyldecanoyloxy)-13-dehydroxyrhizoxin-5b-oic acid
38. rhizoxin-13-yl 9-methyldecanoate
39. 13-(6-ethylnonanoyloxy)-13-dehydroxyrhizoxin-5b-oic acid
40. rhizoxin-13-yl 6-ethylnonanoate
41. 13-dodecanoyloxy-13-dehydroxyrhizoxin-5b-oic acid
42. rhizoxin-13-yl dodecanoate
43. 13-(10-methylundecanoyloxy)-13-dehydroxyrhizoxin-5b-oic acid
44. rhizoxin-13-yl 10-methylundecanoate
45. 13-(6-ethyl-5-methylnonanoyloxy)-13-dehydroxyrhizoxin-5b-oic acid
46. rhizoxin-13-yl 6-ethyl-5-methylnonanoate
47. 13-tridecanoyloxy-13-dehydroxyrhizoxin-5b-oic acid
48. rhizoxin-13-yl tridecanoate
49. 13-(11-methyldodecanoyloxy)-13-dehydroxyrhizoxin-5b-oic acid
50. rhizoxin-13-yl 11-methyldodecanoate
51. 13-(4,6-diethylnonanoyloxy)-13-dehydroxyrhizoxin-5b-oic acid
52. rhizoxin-13-yl 4,6-diethylnonanoate
53. 13-tetradecanoyloxy-13-dehydroxyrhizoxin-5b-oic acid
54. rhizoxin-13-yl tetradecanoate
55. 13-(8-ethyldodecanoyloxy)-13-dehydroxyrhizoxin-5b-oic acid
56. rhizoxin-13-yl 8-ethyldodecanoate
57. 13-pentadecanoyloxy-13-dehydroxyrhizoxin-5b-oic acid
58. rhizoxin-13-yl pentadecanoate
59. 13-(9-ethyltridecanoyloxy)-13-dehydroxyrhizoxin-5b-oic acid
60. rhizoxin-13-yl 9-ethyltridecanoate
61. 13-hexadecanoyloxy-13-dehydroxyrhizoxin-5b-oic acid
62. rhizoxin-13-yl hexadecanoate
63. 13-(8-propyltridecanoyloxy)-13-dehydroxyrhizoxin-5b-oic acid
64. rhizoxin-13-yl 8-propyltridecanoate
65. 13-heptadecanoyloxy-13-dehydroxyrhizoxin-5b-oic acid
66. rhizoxin-13-yl heptadecanoate
67. 13-(7-ethylpentadecanoyloxy)-13-dehydroxyrhizoxin-5b-oic acid
68. rhizoxin-13-yl 7-ethylpentadecanoate
69. 13-octadecanoyloxy-13-dehydroxyrhizoxin-5b-oic acid
70. rhizoxin-13-yl octadecanoate
71. 13-(8-ethylhexadecanoyloxy)-13-dehydroxyrhizoxin-5b-oic acid
72. rhizoxin-13-yl 8-ethylhexadecanoate
73. 13-nonadecanoyloxy-13-dehydroxyrhizoxin-5b-oic acid
74. rhizoxin-13-yl nonadecanoate
75. 13-icosanoyloxy-13-dehydroxyrhizoxin-5b-oic acid
76. rhizoxin-13-yl icosanoate
77. 13-heptanoyloxy-13-dehydroxy-2,3-deoxyrhizoxin-2-en-5b-oic acid
78. 2,3-deoxyrhizoxin-2-en-13-yl heptanoate
79. 13-octanoyloxy-13-dehydroxy-2,3-deoxyrhizoxin-2-en-5b-oic acid
80. 2,3-deoxyrhizoxin-2-en-13-yl octanoate
81. 13-nonanoyloxy-13-dehydroxy-2,3-deoxyrhizoxin-2-en-5b-oic acid
82. 2,3-deoxyrhizoxin-2-en-13-yl nonanoate
83. 13-(7-methyloctanoyloxy)-13-dehydroxy-2,3-deoxyrhizoxin-2-en-5b-oic acid
84. 2,3-deoxyrhizoxin-2-en-13-yl 7-methyloctanoate
85. 13-decanoyloxy-13-dehydroxy-2,3-deoxyrhizoxin-2-en-5b-oic acid
86. 2,3-deoxyrhizoxin-2-en-13-yl decanoate
87. 13-(8-methylnonanoyloxy)-13-dehydroxy-2,3-deoxyrhizoxin-2-en-5b-oic acid
88. 2,3-deoxyrhizoxin-2-en-13-yl 8-methylnonanoate
89. 13-undecanoyloxy-13-dehydroxy-2,3-deoxyrhizoxin-2-en-5b-oic acid
90. 2,3-deoxrthizoxin-2-en-13-yl undecanoate
91. 13-(9-methyldecanoyloxy)-13-dehydroxy-2,3-deoxyrhizoxin-2-en-5b-oic acid
92. 2,3-deoxyrhizoxin-2-en-13-yl 9-methyldecanoate
93. 13-dodecanoyloxy-13-dehydroxy-2,3-deoxrthizoxin-2-en-5b-oic acid
94. 2,3-deoxrthizoxin-2-en-13-yl dodecanoate
95. 13-tridecanoyloxy-13-dehydroxy-2,3-deoxyrhizoxin-2-en-5b-oic acid
96. 2,3-deoxyhizoxin-2-en-13-yl tridecanoate Of the compounds listed above, Compounds Nos. 18, 29, 30, 42 and 54 are particularly preferred.

The compounds of the present invention can exist in the form of various geometrical isomers, depending upon the configuration of the various substituent groups, and also, because of the presence of a number of asymmetric carbon atoms, can exist in the form of various optical isomers. These isomers, and mixtures of these isomers, are all represented herein by a single general formula. However, the present invention embraces both the individual isolated isomers, as well as mixtures thereof. In general, we prefer that the compounds of the invention should have the same configuration as rhizoxin.

The ring-closed lactone derivatives of formula (II) can be produced by reacting the compound of formula (III) defined above, which is either rhizoxin (A represents an oxygen atom) or rhizoxin-2-ene (A represents an extra carbon-carbon bond), with a carboxylic acid of formula (IV) or a reactive derivative thereof. This reaction is a simple and conventional acylation reaction and may be carried out by methods well-known in the art for such acylation reactions.

Where the carboxylic acid of formula (IV) as such is employed, the reaction is preferably effected in the presence of a condensing agent which has a dehydrating activity. Suitable such condensing agents include dicyclohexylcarbodiimide and carbonyldiimidazole. The reaction is preferably effected in the presence of a solvent, the nature of which is not critical, provided that it has no adverse effect on the reaction. Examples of suitable solvents include: aromatic hydrocarbons, such as benzene, toluene or xylene; aliphatic hydrocarbons, such as hexane, heptane, cyclohexane or petroleum ether; halogenated hydrocarbons, especially halogenated aliphatic hydrocarbons, such as chloroform, carbon tetrachloride or methylene chloride; and ethers such as tetrahydrofuran or dioxane. The reaction will take place over a wide range of temperatures and the exact temperature chosen is not critical. We normally find it convenient to carry out the reaction at a temperature in the range from 0° to 40° C., preferably at about room temperature.

Examples of suitable reactive derivatives of the carboxylic acid of formula (IV) include the acid halide, acid anhydrides, mixed acid anhydrides, active esters and active amides, of which the acid halides (such as the acid chloride or acid bromide) and the acid anhydrides (including mixed acid anhydrides) are preferred.

Where an acid halide is employed, the reaction is preferably effected in the presence of an inert solvent and in the presence of an acid-binding agent. The nature of the solvent employed is not critical to the present invention, provided that it has no adverse effect upon the reaction. Preferred solvents are organic solvents, for example: aromatic hydrocarbons, such as benzene, toluene or xylene; halogenated aliphatic hydrocarbons, such as chloroform, methylene chloride or 1,1,2-trichloroethane; ethers, such as diethyl ether, tetrahydrofuran or dioxane; dialkylamides of aliphatic acids, such as dimethylformamide or dimethylacetamide; nitriles, such as acetonitrile; ketones, such as acetone; dimethyl sulfoxide; and pyridine. The function of the acid-binding agent is to remove the hydrogen halide produced in the reaction and any compound capable of reacting with the hydrogen halide and removing it from the reaction system may be employed. Examples of suitable acid-binding agents include: alkali metal hydroxides, such as sodium hydroxide or potassium hydroxide; alkali metal carbonates, such as sodium carbonate or potassium carbonate; and organic bases, such as triethylamine, pyridine, 4-dimethylaminopyridine or 1-methylimidazole. The reaction may be carried out over a wide range of temperatures, but preferably at a temperature from $-10°$ C. to $+130°$ C.

Where an acid anhydride of the compound of formula (IV) is employed, the reaction is preferably effected in the presence of an additional solvent. However, if a sufficient excess of the acid anhydride is used, no additional solvent is necessary. Where a solvent is employed, its nature is not critical, provided that it has no adverse effect upon the reaction. Examples of suitable solvents include: aromatic hydrocarbons, such as benzene, toluene or xylene; and ethers, such as dioxane, tetrahydrofuran and diethylene glycol dimethyl ether. The reaction will take place over a wide range of temperatures, but a temperature within the range from room temperature to 160° C. is preferred.

The product of this reaction is the lactone of formula (II). Pharmaceutically acceptable salts of the carboxylic acid of formula (I) can be prepared by reacting this lactone of formula (II) with a base. This is a conventional reaction for forming a salt from a lactone and may be carried out using techniques well-known in the art.

For example, metal salts of the carboxylic acid of formula (I) can be prepared by reacting the lactone of formula (II) with a hydroxide or carbonate of the appropriate metal, preferably in an aqueous solvent. The nature of this solvent is not critical, provided that it has no adverse effect upon the reaction. Suitable solvents include water itself and mixtures of water with one or more organic solvents, for example: an alcohol, such as methanol or ethanol; an ether, such as ethylene glycol dimethyl ether or dioxane; a ketone, such as acetone; or another solvent such as hexane, ethyl acetate, dimethylformamide, dimethyl sulfoxide or pyridine. A mixture of a hydrophilic organic solvent with water is particularly preferred. The reaction temperature is not critical and we therefore normally prefer to carry out the reaction at about room temperature. However, if desired, it may be conducted whilst gently heating.

In order to avoid opening the lactone formed between the carbon atoms at positions 15 and 1, it is preferred that the ring-opening reaction should take place under relatively mild conditions, e.g. using a relatively dilute solution of the base and/or at relatively low temperatures, e.g. around room temperature.

An amine salt of the carboxylic acid of formula (I) may be prepared by reacting the lactone of formula (II) with an amine, preferably in an aqueous solvent. The solvent employed is not critical, provided that it has no adverse effect upon the reaction. Suitable solvents include water itself and mixtures of water with one or more organic solvents, for example: an alcohol, such as methanol or ethanol; an ether, such as tetrahydrofuran; a nitrile, such as acetonitrile; or a ketone, such as acetone. The preferred solvent is aqueous acetone. The reaction is preferably effected at a pH value of from 7 to 8.5 and, although the reaction temperature is not particularly critical, we prefer a relatively low temperature in order to avoid side reactions. Accordingly, the temperature is preferably below room temperature, more preferably from 5° to 10° C. The reaction goes immediately to completion. The amine salt may also be produced by a salt-exchange reaction, that is to say by adding a mineral acid salt (e.g. the hydrochloride) of the desired amine to an aqueous solution of an metal salt of the compound of formula (I).

An amino acid salt of the carboxylic acid of formula (I) can be prepared by contacting the lactone of formula (II) with an appropriate amino acid, preferably in an aqueous solvent. The solvent employed is not critical, provided that it has no adverse effect upon the reaction. Suitable solvents are aqueous solvents, such as water itself and mixtures of water with one or more organic solvents, for example: an alcohol, such as methanol or ethanol; or an ether, such as tetrahydrofuran. The reaction temperature is not critical, but best results are obtained by heating the reagents, preferably at a temperature of from 50° to 60° C.

The free acids of formula (I) can be prepared by contacting a salt thereof with an acid. The reaction may be carried out by conventional means, as are well-known in this art. For example, the reaction is preferably effected in the presence of a solvent, the nature of which is not critical, provided that it has no adverse effect upon the reaction. Suitable solvents include, for example, methanol, acetone, dimethylformamide and dimethylacetamide. The salt of the carboxylic acid (I) is dissolved in such a solvent, and then a stoichiometric equivalent or a slight excess of an acid is added. There is no particular limitation on the nature of the acid to be used and any organic or inorganic acid may be employed, provided that it does not have any adverse effect upon the desired compound. Suitable acids include trifluroacetic acid, hydrochloric acid and sulfuric acid.

Alternatively, the compounds of formula (I) may be prepared by reacting the ring-opened lactone corresponding to the compound of formula (III) with a compound of formula (IV) or reactive derivative thereof. However, this route is not presently preferred.

The resulting compounds of the invention, prepared by any of the methods described above, can be recovered from the reaction mixtures and, if desired, further purified by any conventional technique or by a combination of such techniques. For example, one suitable recovery procedure comprises: pouring the reaction mixture into water; extracting the product with a waterimmiscible solvent, such as benzene, diethyl ether or ethyl acetate; and then evaporating off the solvent, if necessary after drying the extract, to afford the desired compound. This may, if desired, be purified by an adsorption chromatography technique, using an adsorbent such as activated carbon or silica gel, by ion-exchange chromatography, by gel filtration with a suitable adsorbent, such as Sephadex (trade mark) or by recrystallization from an organic solvent, such as diethyl ether, ethyl acetate or chloroform. Of course, a combination of these techniques may be employed, if appropriate.

The starting material used in the processes of the invention is rhizoxin, which may be prepared by cultivating a rhizoxin-producing fungus, e.g. of the genus Rhizopus, in a culture medium therefor and separating rhizoxin from the cultured broth.

The fungus employed is preferably of the species *Rhizopus chinensis* and is most preferably *Rhizopus chinensis* SANK 21584.

*Rhizopus chinensis* SANK 21584 grows at temperatures ranging from 20° C. to 47° C. It grows very rapidly on the potato-dextrose agar medium at a temperature of 26° C. The floccose mycelia develop well. With the formation of sporangiospores, the color of the hyphae turns from off-white to dark brown. Most of the sporangiospores are unbranched and from one to several of them are formed vertically at the sites where the rhizoids develop with a simple shape.

The size of the sporangiophores is $100-600 \times 7-12$ μm. The sporangia are globose to subglobose, and their size is 50–120 μm; they become brown as they mature. The columellae are subglobose to ellipsoid and the size is 15–50 μm. The sporangiospores are brown and subglobose to ellipsoid and the size is $6-10 \times 3-8$ μm. The clamidospores which are formed take variable shapes. No zygospore is formed.

Identification of strain SANK 21584 was carried out with reference to the following literature, and it was identified to be a strain of *Rhizopus chinensis* Saito;

T. Inui et al, "Taxonomical Studies on Genus Rhizopus", J. Gen. Appl. Microbiol, 11, 1–108 (1965);

D. H. Ellis, "Sporangiospore Ornamentation of Thermophilic Rhizopus Species and Some Allied Genera", Mycologia, 73, 511–523 (1981).

*Rhizopus chinensis* SANK 21584 was deposited with the Fermentation Research Institute, Tokyo, Japan on Feb. 14, 1985 under the accession no. FERM P-8093 and was redeposited under the conditions stipulated by the Budapest Treaty on 15th February 1986 under the accession no. BP-989.

The compounds of the present invention have shown excellent anti-tumor activity against implanted P 388 luekemia cells in mice and can thus be employed as anti-tumor agents against such tumors in animals, especially warm-blooded animals such as humans.

As will be demonstrated hereafter in the biological activity data forming Example 6, the compounds of the invention show an impressive ability to increase the lifespan of test animals experimentally implanted with such tumors, as measured by the Index of Increase in Life Span (ILS). The ILS represents the effect in the animal or patient of a balance between the curative effect of the drug and its toxicity and there is, therefore, not a simple relationship between dosage and ILS. Since a smaller ILS represents a shorter lifespan for the animal or patient (regardless of whether the death is caused by the tumor or the toxicity of the drug), whilst a higher ILS represents a longer lifespan, the critical feature of a potential anti-tumor drug is to maximize its ILS value, regardless of the dosage at which this maximum ILS is reached; in this respect, the criteria for assessing the worth of anti-tumor drugs differ from those used for most other drugs, including antibiotics, hypotensive agents etc. The compounds of the invention show ILS values which indicate a potentially valuable anti-tumor activity coupled with relatively low toxicity and which are significantly better than those of rhizoxin and its known derivatives.

The compounds may be administered by any suitable route, for example the parenteral route (e.g. by intravenous, subcutaneous or intramuscular injection) or by suppository, or by the oral route (for example in the form of a tablet, capsule, powder or granule).

If desired, the compound of the invention may be administered as such, but it is preferably employed in association with a conventional pharmaceutically acceptable carrier or diluent, appropriate to the particular route of administration.

For example, the composition may contain suspending agents, stabilizing agents or dispersing agents and it may be provided as a powder which, prior to administration, is dissolved in a suitable solvent, for example a pyrogen-free sterilized aqueous solvent. Such a powdered preparation may, for example, be produced by pipetting an acetone solution of the compound into a vial, adding water thereto and then lyopholizing the mixture. Compositions for oral use may be provided as tablets, capsules, powders, granules or syrups containing an appropriate amount of the compound of the invention.

Compositions for injection are preferably provided as an ampoule containing a unit dose or as a vial containing multiple doses.

If desired, the compounds of the invention may be used together with other anti-cancer agents, for example drugs of the nitrosourea series, such as ACNU or BCNU, cisplastin, 5-FU, daunomycin, adriamycin, mitomycin C or etoposide.

The dosage of the compounds of the invention will vary, depending upon the severity and nature of the disease, as well as the route, frequency and period of administration. However, a suitable dose for an adult human would be in the range of from 1 to 100 mg per day, which may be administered in a single dose or in divided doses.

The preparation and biological activity of the compounds of the present invention are further illustrated by the following Examples.

EXAMPLE 1

Rhizoxin-13-yl Decanoate (Compound No. 30)

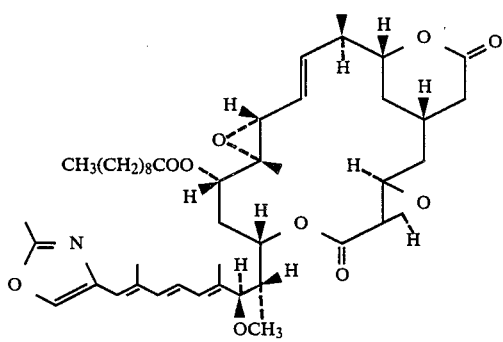

250 mg (3.0 mmole) of pyridine and a catalytic amount of 4-dimethylaminopyridine were added, whilst ice-cooling, to a solution of 625 mg (1 mmole) of rhizoxin and 285 mg (1.5 mmole) of decanoyl chloride in 10 ml of benzene, and the mixture was agitated at room temperature for about 30 minutes. At the end of this time, the reaction mixture was washed, in turn, with dilute hydrochloric acid and then water. It was then dried over anhydrous sodium sulfate, and the solvent was removed by evaporation under reduced pressure. The residue was then purified by silica gel column chromatography, eluted with a 95:5 by volume mixture of benzene and acetone, to afford a crystalline compound, which was recrystallized from methanol to give about 500 mg of the title compound as white crystals melting at 168°–169° C.

Ultraviolet Absorption Spectrum (CH$_3$OH) $\lambda_{max}$nm ($\epsilon$): 297 (43,700), 309 (55,800), 323 (41,100).

Infrared Absorption Spectrum (CCl$_4$) $\nu_{max}$cm$^{-1}$: 2940, 2855, 1740, 1580, 1450, 1225, 1190, 1110, 1090.

Electron impact mass spectrum: 779 (M+), 232.

EXAMPLE 2

Following the same procedure as described in Example 1, but employing different acid chlorides, the following compounds were also prepared:

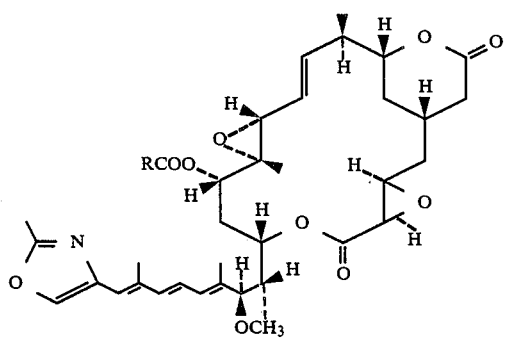

(1) Rhizoxin-13-yl butyrate (Compound No. 2)
R=—CH$_2$CH$_2$CH$_3$;
White powder:
Ultraviolet Absorption Spectrum (CH$_3$OH) $\lambda_{max}$nm($\epsilon$): 297 (44,400), 309 (56,600), 323 (41,700).

Infrared Absorption Spectrum (CCl$_4$) $\nu_{max}$cm$^{-1}$: 2970, 2940, 2870, 1740, 1580, 1450, 1380, 1225, 1190, 1175, 1110, 1090.

Electron impact mass spectrum: 625 (M+), 232 (C-17 to C-26a segment).

(2) Rhizoxin-13-yl isovalerate (Compound No. 6)
R=—CH$_2$CH(CH$_3$)$_2$:
White powder:
Ultraviolet Absorption Spectrum (CH$_3$OH) $\lambda_{max}$nm ($\epsilon$): 297 (42,800), 309 (55,200), 323 (40,300).

Infrared Absorption Spectrum (CCl$_4$) $\nu_{max}$cm$^{-1}$: 2970, 2940, 2870, 1740, 1580, 1460, 1225, 1190, 1110, 1090.

Electron impact mass spectrum: 751 (M+), 232.

(3) Rhizoxin-13-yl octanoate (Compound No. 18)
R=—(CH$_2$)$_6$CH$_3$:
White powder:
Ultraviolet Absorption Spectrum (CH$_3$OH) $\lambda_{max}$nm ($\epsilon$): 297 (43,400), 309 (55,200), 323 (40,700).

Infrared Absorption Spectrum (CCl$_4$) $\nu_{max}$cm$^{-1}$: 2970, 2940, 2855, 1740, 1580, 1450, 1225, 1190, 1110, 1090.

Electron impact mass spectrum: 751 (M+), 232.

(4) Rhizoxin-13-yl dodecanoate (Compound No. 42)
R=—(CH$_2$)$_{10}$CH$_3$:
white crystals, melting at 141°–142° C.

Ultraviolet Absorption Spectrum (CH$_3$OH) $\lambda_{max}$nm ($\epsilon$): 296 (42,800), 309 (54,600), 323 (40,300).

Infrared Absorption Spectrum (CCl$_4$) $\nu_{max}$cm$^{-1}$: 2940, 2855, 1740, 1580, 1455, 1225, 1190, 1110, 1090.

Electron impact mass spectrum: 807 (M+), 232.

(5) Rhizoxin-13-yl octadecanoate (Compound No. 70)
R=—(CH$_2$)$_{16}$CH$_3$:
White crystals, melting at 62°–64° C.

Ultraviolet Absorption Spectrum (CH$_3$OH) $\lambda_{max}$nm ($\epsilon$): 297 (40,500), 309 (51,500), 323 (38,100).

Infrared Absorption Spectrum (CCl$_4$) $\nu_{max}$cm$^{-1}$: 2940, 2855, 1740, 1580, 1455, 1225, 1190, 1110, 1090.

Electron impact mass spectrum: 891 (M+), 232.

(6) Rhizoxin-13-yl tetradecanoate (Compound No. 54)
R=—(CH$_2$)$_{12}$CH$_3$:
White crystals, melting at 116.5°–117.5° C.

Ultraviolet Absorption Spectrum (ethanol) $\lambda_{max}$nm ($\epsilon$): 298 (41800), 310 (53400), 324 (39800).

Infrared Absorption Spectrum (KBr) $\nu_{max}$cm$^{-1}$: 2925, 2853, 1736, 1231, 1187, 1109, 1084, 983.

Electron impact mass spectrum: 835 (M+), 232.

EXAMPLE 3

Sodium 13-decanoyloxy-13-dehydroxyrhizoxin-5b-oate
(Sodium salt of Compound No. 29)

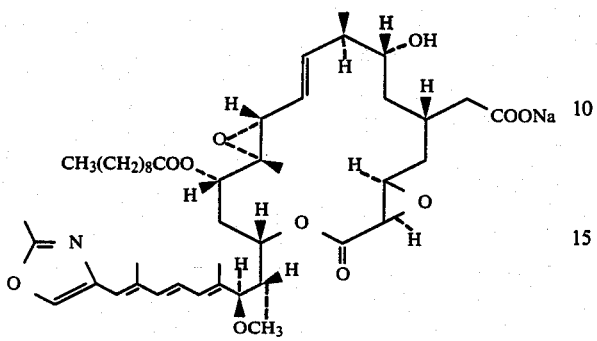

2 ml (0.2 mmole) of a 0.1N aqueous solution of sodium hydroxide were added dropwise, whilst stirring, to a solution of 156 mg (0.2 mmole) of rhizoxin-13-yl decanoate (prepared as described in Example 1) in 8 ml of ethylene glycol dimethyl ether, and the mixture was agitated at room temperature for 10 minutes. The organic solvent was then evaporated off under reduced pressure at room temperature, and the residual aqueous solution was lyophilized, to give 164 mg of the title compound as a white powder melting at 115°–120° C.

Ultraviolet Absorption Spectrum (CH3OH) $\lambda_{max}$nm ($\epsilon$): 297 (40,200), 309 (51,500), 323 (37,900).

Infrared Absorption Spectrum (CCl4) $\nu_{max}$cm$^{-1}$: 3300 (broad), 2940, 2855, 1740, 1575, 1450, 1410, 1190, 1110, 1090.

Electron impact mass spectrum: 780 (M+-ONa), 779 (M+-HONa), 232 (base peak).

EXAMPLE 4

13-Decanoyloxy-13-dehydroxyrhizoxin-5b-oic acid
(Compound No. 29)

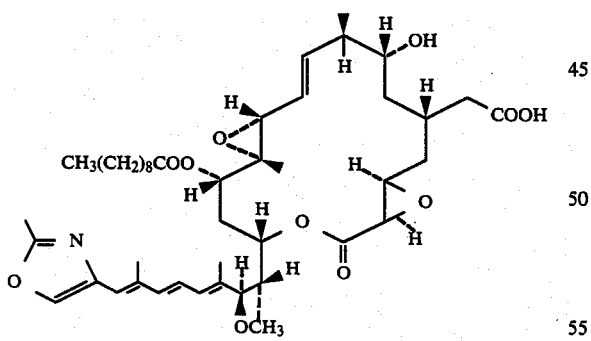

A sample of the sodium 13-decanoyloxy-13-dehydroxyrhizoxin-5b-oate (prepared as described in Example 3) was dissolved in methanol, and 1.1 equivalents of 0.1N aqueous hydrochloric acid were added thereto. The mixture was then subjected to thin layer chromatography (Kiesel gel 60 F-254, Merck) and showed a spot corresponding to the free carboxylic acid, the title compound. Using as the developing solvent a 4:1 by volume mixture of benzene and isopropanol, the Rf value was 0.40; using as developing solvent a 1:1 by volume mixture of benzene and acetone, the Rf value was 0.23. For comparison, the Rf values of rhizoxin in these developing solvents are 0.82 and 0.89, respectively.

EXAMPLE 5

2,3-Deoxyrhizoxin-2-en-13-yl decanoate (Compound No. 86)

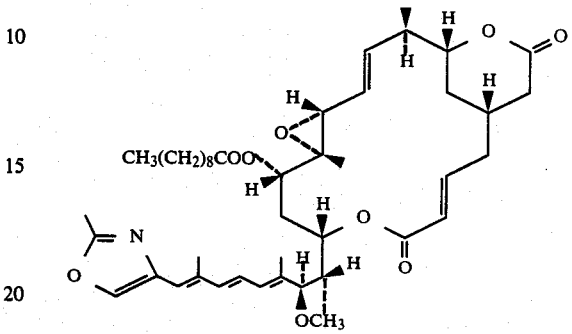

183 mg (0.3 mmole) of rhizoxin-2-ene (prepared as described hereafter in the Preparation), 100 mg (0.99 mmole) of triethylamine and a catalytic amount of 4-dimethylaminopyridine were dissolved in 10 ml of dry benzene, and then 86 mg (0.45 mmole) of decanoyl chloride were added dropwise, whilst stirring and ice-cooling, to the resulting solution. Stirring was continued for a further 1 hour at room temperature, and then the reaction mixture was washed with water and dried over anhydrous magnesium sulfate. The solvent was then removed by evaporation under reduced pressure. The residue was subjected to silica gel column chromatography, eluted with a 95:5 by volume mixture of benzene and acetone, to give crude crystals, which were recrystallized from methanol, giving 165 mg of the title compound as white crystals, melting at 145°–146° C.

Ultraviolet Absorption Spectrum (CH3OH) $\nu_{max}$nm ($\epsilon$): 297 (44,000), 309 (56,900), 323 (41,500).

Infrared Absorption Spectrum (CCl4) $\nu_{max}$cm$^{-1}$: 2940, 2855, 1735, 1650, 1580, 1450, 1380, 1320, 1210, 1195, 1170, 1110, 1080, 1040, 980, 965.

Electron impact mass spectrum: 763 (M+), 232 (base peak).

PREPARATION

Rhizoxin-2-ene

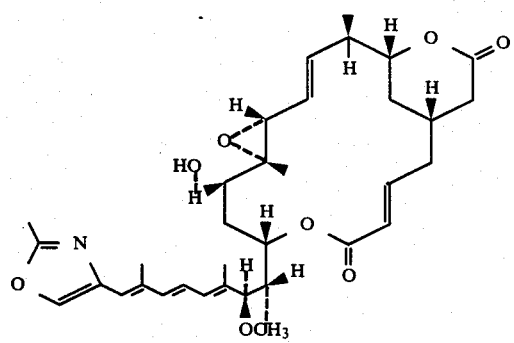

A slant-full of hyphae from a culture of *Rhizopus chinensis* (FERM-8093) was inoculated into a 500 ml Erlenmeyer flask containing 100 ml of a culture medium having the following composition (percentages are by weight):

| | |
|---|---|
| Glucose | 1% |
| Lactose | 1% |
| Polypeptone | 1% |
| KH$_2$PO$_4$ | 0.25% |
| K$_2$HPO$_4$ | 0.75% |
| MgSO$_4$.7H$_2$O | 0.25% |
| (NH$_4$)$_2$SO$_4$ | 0.2% | pH (before sterilization) 6.8 (which had previously been sterilized at 120° C. for 45 minutes). Cultivation was carried out at 28° C. for 24 hours, with shaking.

200 ml of the resulting pre-incubated fluid were then transferred to a 500 liter culture jar containing 30 liters of a medium having the composition described above, and the mixture was cultured for 95 hours at 28° C. under aeration at the rate of 15 liters per minute, with stirring at 200 rpm and under an internal pressure of 1.0 kg/cm$^2$.

At the end of this time, the cultured broth was filtered, with the aid of a Celite (trade mark) filter aid, and the filtrate was extracted with an equal volume of ethyl acetate. The solvent was evaporated from the extract, and the residue was subjected to LH20 column chromatography, using acetone as the eluent, to give a fraction containing the title compound. This fraction was then subjected to silica gel column chromatography, using a 85:15 by volume mixture of benzene and acetone as eluent, to give a mixture of the title compound and rhizoxin. Further purification of the mixture using LH20 column chromatography and silica gel column chromatography gave 15 mg of the title compound of about 90% purity and 670 mg of rhizoxin of the same approximate purity from 300 liters of cultured broth. The title compound was finally purified with high pressure liquid chromatography, using ODS, to give the title compound as a white powder, melting at 125°–128° C.

Ultraviolet Absorption Spectrum (CH$_3$OH) $\lambda_{max}$nm ($\epsilon$): 297 (48,600), 309 (64,400), 323 (46,300).

Infrared Absorption Spectrum (CCl$_4$) $\nu_{max}$cm$^{-1}$: 3580, 2970, 2940, 2880, 1740, 1720, 1650, 1580, 1450, 1385, 1320, 1310, 1220, 1195, 1170, 1110, 1080, 1050, 980, 965.

Electron impact mass spectrum: 609 (M+), 232 (base peak).

EXAMPLE 6

Biological Activity

The test animals employed were female mice, 8 weeks of age, of the CDF$_1$ strain. The mice were divided into groups, each of 5 mice, and all mice within the group were treated identically. Into each mouse was implanted intraperitoneally 1×10$^6$ cells of the mouse leukemia p-388.

The test compounds shown in the following Table were suspended in sterilized physiological saline and the suspension was administered intraperitoneally on the first, fifth and ninth days following implantation of the leukemia cells. The period for which the mice survived was determined. A control group was treated identically, except that no active compound was administered.

The anti-tumor effect is shown in the following Table as the increase in life span [ILS (%)], calculated from the following equation:

ILS (%) = (Dt/Dc − 1) × 100 where
Dt = average number of days survival by the test group; and
Dc = average number of days survival by the control group.

In this test, Dc was 10.6 days.

The compounds of the invention are identified in the following Table by the numbers assigned to them in the foregoing list. Compounds A, B and C are rhizoxin, rhizoxin-2-ene and rhizoxin-13-yl acetate.

TABLE

| Cpd. No. | Dose (mg/kg/day) | | | | | | | |
|---|---|---|---|---|---|---|---|---|
| | 64 | 32 | 16 | 8 | 6 | 4 | 2 | 1 |
| A | — | — | — | — | −46 | 34 | 73 | 50 |
| B | — | — | −37 | 65 | — | 17 | 27 | — |
| C | — | — | — | — | — | 38 | 34 | — |
| 2 | — | — | — | 140 | — | 62 | 42 | — |
| 6 | — | — | — | 98 | — | 38 | 15 | — |
| 18 | — | — | — | 241 | — | 122 | 45 | 14 |
| 29 | 140 | 72 | 67 | 22 | — | 37 | — | — |
| 30 | — | — | — | 214 | — | 188 | 78 | 27 |
| 42 | — | — | — | 145 | — | 143 | 76 | 33 |
| 54 | — | — | — | 145 | — | 200 | 61 | 51 |

The results shown above indicate a significant anti-tumor activity in the compounds of the present invention. All of the compounds of the invention have an ILS value within the range from 98 to 241 at least at one dosage level, indicating a significantly better degree of anti-tumor activity than rhizoxin, rhizoxin-2-ene and rhizoxin-13-yl acetate, where the highest values were 73 (at 2 mg/kg/day), 65 (at 8 mg/kg/day) and 38 (at 4 mg/kg/day), respectively. A negative ILS indicates that the average lifespan of the test group was less than that of the control group. Thus, rhizoxin showed its highest ILS at 2 mg/kg/day but, by a dose of 6 mg/kg/day, the toxicity of rhizoxin predominated over its anti-tumor activity. On the other hand, Compound No. 29 did not reach its maximum ILS value until a dose (of those tried) of 64 mg/kg/day and the majority of the other compounds of the invention showed their maximum ILS values at doses of 8 mg/kg/day.

We claim:
1. A compound of formula (I):

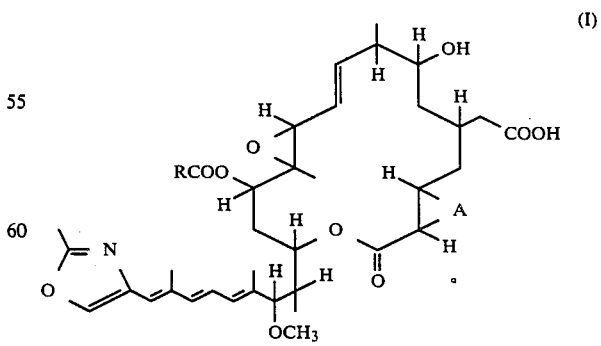

wherein:
R represents an alkyl group having 2–30 carbon atoms; and

A represents an extra carbon-carbon bond or an oxygen atom,
and pharmaceutically acceptable salts and ring-closed lactones thereof.

2. The compound as claimed in claim 1, wherein R represents a $C_3$–$C_{17}$ alkyl group.

3. The compound as claimed in claim 1, wherein R represents a $C_7$–$C_{13}$ alkyl group.

4. The compound as claimed in claim 1, wherein R represents an alkyl group selected from the group consisting of heptyl, nonyl, undecyl and tridecyl groups.

5. The compound as claimed in claim 1, wherein R represents an alkyl group selected from the group consisting of heptyl, nonyl, undecyl and tridecyl groups and A represents an oxygen atom.

6. The compound as claimed in claim 1 wherein R represents a $C_2$–$C_{24}$ alkyl group.

7. A compound of formula (II):

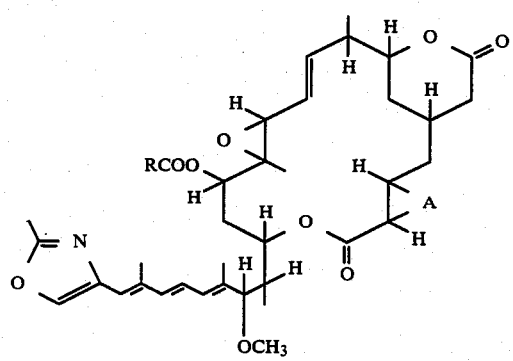

wherein:
R represents an alkyl group having 2–30 carbon atoms; and
A represents an extra carbon-carbon bond or an oxygen atom.

8. The compound as claimed in claim 7 wherein R represents a $C_2$–$C_{24}$ alkyl group.

9. The compound as claimed in claim 7, wherein R represents a $C_3$–$C_{17}$ alkyl group.

10. The compound as claimed in claim 7, wherein R represents a $C_7$–$C_{13}$ alkyl group.

11. The compound as claimed in claim 7, wherein R represents an alkyl group selected from the group consisting of heptyl, nonyl, undecyl and tridecyl groups.

12. The compound as claimed in claim 7 wherein R represents an alkyl group selected from the group consisting of heptyl, nonyl, undecyl and tridecyl groups and A represents an oxygen atom.

13. The compound of claim 7 which is Rhizoxin-13-yl octanoate.

14. The compound of claim 1 which is 13-Decanoyloxy-13-dehydroxyrhizoxin-5b-oic acid and pharmaceutically acceptable salts thereof.

15. The compound of claim 7 which is Rhizoxin-13-yl decanoate.

16. The compound of claim 7 which is Rhizoxin-13-yl dodecanoate.

17. The compound of claim 7 which is Rhizoxin-13-yl tetradecanoate.

18. A pharmaceutical composition comprising an anti-tumor agent in admixture with a pharmaceutically acceptable carrier or diluent, wherein the anti-tumor agent is selected from the group consisting of compounds of formula (I):

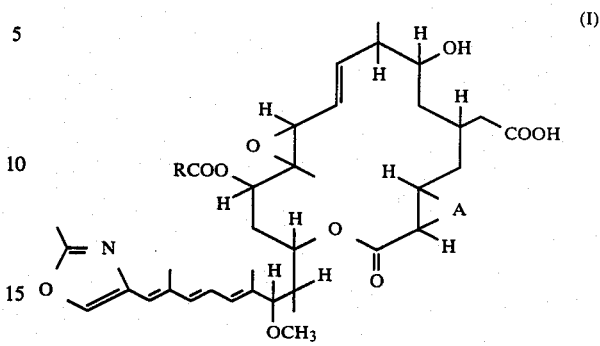

wherein:
R represents an alkyl group having 2–30 carbon atoms; and
A represents an extra carbon-carbon bond or an oxygen atom,
and pharmaceutically acceptable salts and ring-closed lactones thereof.

19. A composition as claimed in claim 18, wherein R represents a $C_3$–$C_{17}$ alkyl group.

20. A composition as claimed in claim 18, wherein R represents a $C_7$–$C_{13}$ alkyl group.

21. A composition as claimed in claim 18, wherein R represents an alkyl group selected from the group consisting of heptyl, nonyl, undecyl and tridecyl groups.

22. A composition as claimed in claim 18, wherein R represents an alkyl group selected from the group consisting of heptyl, nonyl, undecyl and tridecyl groups and A represents an oxygen atom.

23. A composition as claimed in claim 18, wherein said lactone is a compound of formula (II):

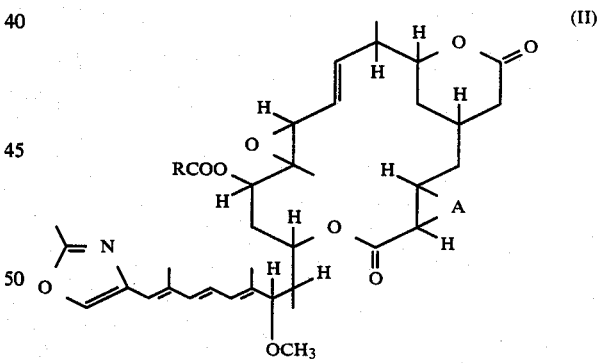

wherein R and A are as defined in claim 18.

24. A composition as claimed in claim 23, wherein R represents a $C_3$–$C_{17}$ alkyl group.

25. A composition as claimed in claim 1, wherein R represents a $C_7$–$C_{13}$ alkyl group.

26. A composition as claimed in claim 23, wherein R represents an alkyl group selected from the group consisting of heptyl, nonyl, undecyl and tridecyl groups.

27. A composition as claimed in claim 23, wherein R represents an alkyl group selected from the group consisting of heptyl, nonyl, undecyl and tridecyl groups and A represents an oxygen atom.

* * * * *

UNITED STATES PATENT AND TRADEMARK OFFICE
CERTIFICATE OF CORRECTION

PATENT NO. : 4,791,128

DATED : December 13, 1988

INVENTOR(S) : OKUDA et al

It is certified that error appears in the above-identified patent and that said Letters Patent is hereby corrected as shown below:

Column 18, line 58 (Claim 25):  Replace "claim 1" with

--claim 23--.

Signed and Sealed this

Twenty-fifth Day of February, 1992

*Attest:*

HARRY F. MANBECK, JR.

*Attesting Officer*  *Commissioner of Patents and Trademarks*